United States Patent [19]

Au et al.

[11] Patent Number: 5,296,588

[45] Date of Patent: Mar. 22, 1994

[54] PROCESS OF PREPARING N-SUBSTITUTED ALDONAMIDES

[75] Inventors: Van Au, Peekskill, N.Y.; Bijan Harirchian, South Orange, N.J.

[73] Assignee: Lever Brothers Company, Division of Conopco, Inc., New York, N.Y.

[21] Appl. No.: 958,402

[22] Filed: Oct. 8, 1992

Related U.S. Application Data

[63] Continuation-in-part of Ser. No. 816,422, Dec. 31, 1991, abandoned.

[51] Int. Cl.$^5$ .................. C07G 3/00; C07H 15/04; C07C 235/06
[52] U.S. Cl. .................. 536/1.11; 536/4.1; 536/22.1; 536/124
[58] Field of Search .......... 536/1.11, 22, 124, 4.1, 536/22.1

[56] References Cited

U.S. PATENT DOCUMENTS

| | | | |
|---|---|---|---|
| 2,662,073 | 12/1953 | Mehltretter et al. | 536/53 |
| 2,746,916 | 5/1956 | Magariello | 536/53 |
| 2,752,334 | 6/1956 | Walton | 536/53 |
| 4,774,231 | 9/1988 | Petitou et al. | 514/53 |

FOREIGN PATENT DOCUMENTS 2227008  11/1974  France .

OTHER PUBLICATIONS

Grant et al, eds. Grant & Hackh's Chemical Dictionary, McGraw-Hill Book Company, New York, 1987, p. 21.
European Search Report in European Patent Application 92204033.2.
Derwent Abstract of FR 2.227.008.
Taravel, Francois R. "Amphiphilic properties of synthetic glycolipids based on amide linkages, 4". Makromol. Chem. vol. 191 (1990), pp. 3097–3106.
Patent Abstracts of Japan, vol. 015163, JP 3034946.
Ullmann's Encyclopedia of Industrial Chemistry. vol. A14: Immobilized Biocatalysts to Isoprene, (1989), pp. 448–449.
Williams, Taffy J., et al. "A New Class of Model Glycolipids: Synthesis, Characterization, and Interaction with Lectins." Archives of Biochemistry and biophysics, vol. 195, No. 1, (Jun. 1979), pp. 145–151.
Kobayashi, Kazukiyo, et al. "Synthesis and Functions of Polystyrene Derivatives Having Pendant Oligosaccharides." Polymer Journal, vol. 17, No. 4, (1985), pp. 567–575.
Ziegast, Gerd et al., "Coupling of mono- and oligosaccharides to α-w-diamino substituted poly(oxyethylene) and multifunctional amines by amide linkage." Makromol. Chem., Rapid Commun. vol. 5, (1984), pp. 373, 379.

*Primary Examiner*—Nathan M. Nutter
*Attorney, Agent, or Firm*—Rimma Mitelman

[57] ABSTRACT

A process of preparing aldonamides and N-substituted aldonamides which includes the steps of recovering a by-product of the process (an ammonium salt of an aldonic acid) and converting it into at least one starting material. Aldonolactone is reacted with a primary or secondary amine and the resulting solution containing the by-product of the reaction is treated with a solid base to obtain a solid aldonate salt and a second solution containing the starting amine and some aldonamide. The second solution may be recycled as part of the starting material mixture. Alternatively, the amine and the aldonamide may be recovered from the second solution, and the amine alone may be recycled. The solid salt of aldonic acid may be converted into aldonic acid, which in turn may be converted into aldonolactone. The obtained aldono-1,5-lactone may also be utilized as a starting ingredient in the synthesis according to the present invention.

17 Claims, No Drawings

PROCESS OF PREPARING N-SUBSTITUTED ALDONAMIDES

This is a continuation-in-part of copending application Ser. No. 07/816,422, filed Dec. 31, 1991 and now abandoned.

FIELD OF THE INVENTION

The invention relates to an improved process of preparing N-substituted aldonamides.

RELATED ART

An aldonamide is defined as the amide of an aldonic acid and an aldonic acid in turn is defined as a sugar substance (e.g., any cyclic sugar) in which the aldehyde group (generally found at the $C_1$ position on the sugar) has been replaced by a carboxylic acid. Aldonamides may be based on compounds comprising one saccharide unit (e.g., gluconamide), two saccharide units (in which case aldonamides are termed aldobionamides, e.g., lactobionamide or maltobionamide) or they may be based on compounds comprising more than two saccharide units, as long as the polysaccharide has a terminal sugar unit with an aldehyde group available for oxidation.

Walton et al. (U.S. Pat. No. 2,752,334) discloses a process for the preparation of the N-substituted lactobionamides by reacting the corresponding organic primary or secondary amine with lactobiono-1,5-lactone. The reaction is effected by heating the reactants with a solvent in the case of the amines having a higher boiling point. However, the use of a solvent and lower temperature is said to give better yields with less chance of decomposition in the course of the reaction and therefore a purer product. Reaction temperatures within the rang from 65° to 140° C. are said to be preferred. Yields of from 70 to 75% were reported.

Kobayashi et al., "Synthesis and Functions of Polystyrene Derivatives Having Pendant Oligosaccharides," Polymer Journal, Vol. 17, No. 4, 567–575 (1985), describe a process wherein a lactone is dissolved in refluxing methanol and a solution of amine in ethanol is added. The mixed solution is refluxed for two hours. 82% yield was reported.

Williams et al., "A new Class of Glycolipids: Synthesis, Characterization, and Interaction with Lectins," Archives of Biochemistry and Biophysics, Vol. 195, No. 1, June, 145–151, 1979, describe a process wherein a lactone was dissolved in methanol by gentle heating, an amine was added, and the reaction mixture was stirred overnight at room temperature. 70% yield was reported.

Ziegast et al., "Coupling of Mono- and Oligosaccharides to δ-w-diamino substituted Poly(oxyethylene) and Multifunctional Amines by Amide Linkage", Makromol Chem., Rapid Commun. 5, 313–379 (1984) disclose the procedure for coupling of carbohydrates to various compounds: saccharide is converted into the aldonic acid lactone via electrolytic oxidation and subsequent binding to an amino group containing carrier by amide linkage. The reaction according to Ziegast et al. requires an excess of lactone, which is subsequently separated by using relatively strong basic ion exchange column. Ziegast et al. employ an excess of lactone and conduct the reaction at 70° C. or above.

Aldonamides are carbohydrate-based molecules and, as such, represent a source of renewable raw materials that are synthetically versatile and environmentally friendly. Aldonamides have useful physical properties (e.g., surfactancy) which makes them suitable for many applications in personal care, dental, detergent and cosmetic areas. Surfactant compositions incorporating aldonamides have been described in a co-pending commonly assigned application, Ser. No. 07/816,419, incorporated by reference herein and now abandoned. In light of a potentially large demand for aldonamides, it is desirable to improve the efficacy of processes of their production. Prior art processes discussed above result in formation of 20–30% of by-products, which have not been utilized or identified.

Accordingly, it is an object of the invention to provide an improved process of manufacturing aldonamides.

It is another object of the invention to provide a process of preparing aldonamides wherein a by-product of the process is converted to at least one starting material required in the process.

It is yet another object of the invention to provide a continuous process of preparing aldonamides.

These and other objects of the invention will become more apparent from the detailed description and examples that follow.

SUMMARY OF THE INVENTION

The above objects are accomplished by the present invention which includes a process of preparing an N-substituted aldonamide, the process including the steps of:

i) preparing a homogeneous mixture containing an aldonolactone, an organic polar solvent, and an amine $HNR^1R^2$, wherein $R^1$ and $R^2$ are the same or different and may contain heteroatoms and are selected from the group consisting of hydrogen, an aliphatic hydrocarbon radical, an aromatic radical, a cycloaliphatic radical, an amino acid ester, an ether amine and mixtures thereof, except that $R^1$ and $R^2$ are not both hydrogen at the same time, wherein the molar ratio of the aldonolactone to the amine is in the range of from 1:1.5 to 1:1;

ii) reacting the homogeneous mixture at a temperature not greater than 65° C. to obtain a reaction product including a solution comprising the aldonamide and a corresponding ammonium salt of an aldonic acid; and iii) treating the solution with a solid base to obtain a second solution containing the starting amine and the aldonamide.

Step (iii) of the inventive process is conducted with an objective to recover from the solution obtained in step (ii) at least one starting ingredient. An alternative process which attains the same objective is disclosed in a co-pending commonly assigned application, Ser. No. 07/816,422. According to the process disclosed in the '422 application, the solution obtained in step (ii) is passed through an anionic exchange column and the column is eluted with an organic polar solvent to obtain an eluate containing the starting amine and the aldonamide.

The process disclosed in the '422 application and the process according to the present invention are improved compared to the prior art processes for the preparation of aldonamides, because both processes convert a previously unidentified and unutilized by-product, the ammonium salt of an aldonic acid into one or more compounds which may be employed in a variety of reactions. Preferably, the resulting compounds are employed as starting materials (i.e., recycled) in the preparation of aldonamides, in which case the aldonamides may be synthesized via a continuous process.

The process according to the present invention is preferred over the process disclosed in the '422 application because the process results in the formation of a solid salt of an aldonic acid which may be isolated directly from the solution without the need for resin treatment.

The solution obtained in step (iii) may be recycled as part of the starting material mixture, although the solution contains aldonamide which is not a required starting ingredient. Alternatively, the amine and the aldonamide may be recovered from the solution, and the amine alone or the amine and the organic solvent may be recycled, without the aldonamide.

Preferably, the process according to the present invention is continued to recover an aldonic acid: in step (iii), besides the solution containing an amine and an aldonamide, a precipitate, i.e., a solid salt of an aldonic acid is formed which salt may be isolated by filtration. This salt may be converted to the aldonic acid, which may in turn be converted to the aldonolactone utilized as a starting ingredient in the inventive process.

Any N-substituted aldonamide may be synthesized according to the present process, as long as a particular primary or secondary amine $HNR^1R^2$ required to produce that aldonamide is available commercially or can be synthesized.

DETAILED DESCRIPTION OF THE INVENTION

The inventive process is suitable for synthesis of any N-substituted aldonamide. Examples of aldonamides include but are not limited to lactobionamides, maltobionamides, cellobionamides, melibionamides, gentiobionamides and the like.

Starting materials employed in the inventive processes include an aldonolactone, a primary or secondary amine carrying the desired $R^1$ and $R^2$ groups, and an organic polar solvent. Any organic polar solvent is suitable, for example aliphatic alcohols, glycols and glycol monoethers, such as methanol, ethanol, isopropanol, ethylene glycol, polyethylene glycol, triethylene glycol, diethylene glycol, diethylene glycol monoethyl ether, ethylene glycol monobutyl ether, ethylene glycol monoethyl ether, ethylene glycol monomethyl ether, diethylene glycol monobutyl ether, and triethylene glycol monomethyl ether. Of course, other polar solvents not listed above may be employed.

Aldonolactone is defined as a lactone of an aldonic acid.

Aldonolactones may be obtained commercially, (e.g., from Aldrich Chemicals) or they may be prepared by dissolving an aldonic acid in an organic solvent such as dioxane or methanol. Preparation of aldonolactones is described in a greater detail by Williams et al., "A new Class of Glycolipids: Synthesis, Characterization, and Interaction with Lectins," Archives of Biochemistry and Biophysics, Vol. 195, No. 1, June, 145–151, 1979 and by H. S. Isbell, Bureau of Standards, Journal of Research, Vol. 11, 1933 which disclosures are incorporated by reference herein. Alternatively, aldonolactones may be obtained by spray drying an aqueous solution as described in U.S. Pat. No. 2,746,916, incorporated by reference herein. An aldonolactone preferably employed in the present invention is an aldono-1,5-lactone.

The amine, $HNR^1R^2$, may be obtained commercially (Aldrich Chemicals) as in the case of aliphatic amine, or from Sherex as in the case of alkyloxy alkylamine (e.g., alkyloxypropyl amine [Adogen 180®]) or it may be synthesized. When aliphatic amines are employed $R^1$ and/or $R^2$ contain at least 3 carbon atoms to ease synthesis (amines wherein $R^1$ and/or $R^2$ contain fewer than 3 carbon atoms have to be bubbled in due to their high volatility).

An example of the reaction employed in the inventive synthesis is as follows:

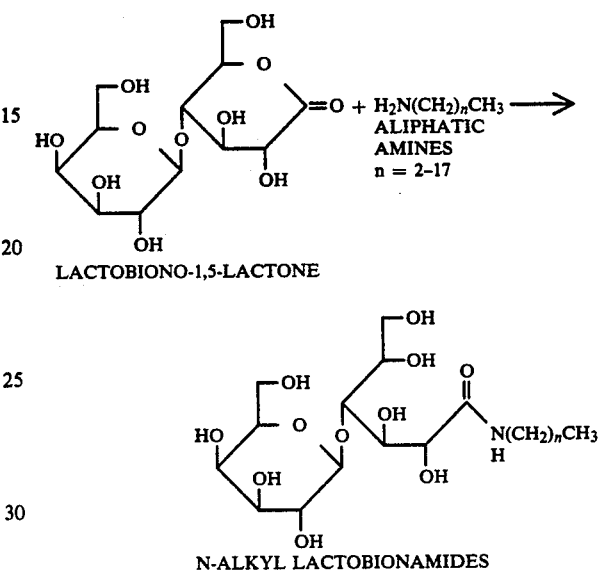

LACTOBIONO-1,5-LACTONE

N-ALKYL LACTOBIONAMIDES

The aldonolactone and the amine constitute 10–50% by weight of the starting reaction mixture, and the solvent constitutes 50–90% by weight. Preferably, the aldonolactone and the amine constitute from about 20% to about 40% of the starting reaction mixture. The molar ratio of the aldonolactone to the amine is in the range of from 1:1.5 to 1:1, preferably in the range of from 1:1.3 to 1:1. Most preferably, the molar ratio of the aldonolactone to the amine in the starting reaction mixture is 1:1.

In the first step of the inventive process a homogeneous mixture of starting materials is prepared. Preferably, in order to facilitate the formation of the homogeneous mixture the solvent is slightly heated, typically to a temperature in the range of from 25° to 65° C., preferably in the range of from about 25° C. to 50° C.

It is preferred, in order to optimize purity, that a mixture of the aldonolactone in the solvent is prepared first, with stirring, preferably in a warm solvent. The aldonolactone may be completely dissolved in the solvent, although more frequently only a partial dissolution occurs. The amine, $HNR^1R^2$, is subsequently added, with stirring, preferably gradually or in several portions, in order to attain the homogeneity of the mixture and to optimize the purity of the product. The stirring is conducted with a magnetic stirrer or with an overhead stirrer at moderate rpm. The amine may be added neat (i.e., liquid or melted) or it may be added as a solution in the same solvent that was combined with the aldonolactone.

The resulting homogeneous mixture is reacted to obtain a reaction product including a solution containing at least some of the product, N-substituted aldonamide and a by-product, a corresponding ammonium salt of an aldonic acid. The stirring is typically continued at the same rate as that employed during the mixing step. The reaction may be conducted at room temperature or at an increased temperature. Typically, the reaction temperature is in the range of from about 25° C. to about 65° C., preferably in the range of from about 25° C. to about 50° C., most preferably in the range of from about 25° C. to about 40° C. It is essential to carry out the reaction at a temperature not greater than 65° C. in order to minimize heat decomposition as well as base induced β-elimination. For the same reason, it is important that in the first (mixing) step the temperature does not exceed 65° C. either. Best results are obtained at temperatures not greater than 60° C., most preferably not greater than 50° C.

The product, N-substituted aldonamide, may or may not precipitate out of solution. Typically, at least part of N-substituted aldonamide is present in the solution. When the precipitate is formed, it is separated from the solution. The separation may be conveniently carried out by filtering the precipitate out (by gravity or vacuum filtration), although other separation techniques, e.g. centrifugation, may be employed. The product, N-substituted aldonamide, is washed with a suitable solvent and dried. The inventive process typically results in yields of N-substituted aldonamides in the range of from about 80% to about 95%. Further steps of the inventive process are carried out on the obtained solution.

The present invention is based, in part, on the discovery that a by-product contained in the solution consists predominantly of an ammonium salt of aldonic acid: the ammonium salt typically constitutes from about 5% to about 20% by weight of the solid contained in the solution. The inventive process aims to convert the by-product into compounds which may be used as starting materials in a variety of reactions. The by-product is preferably converted into the starting materials for the inventive process, i.e., the aldonolactone and the amine.

According to the inventive process, the solution obtained in step (ii) is treated with a solid base. Examples of suitable bases include but are not limited to alkali or alkaline earth metal bicarbonate or carbonate salts and alkali or alkaline earth hydroxides, metal alkoxides and mixtures thereof. In the case of carbonate or bicarbonate, the base is preferably in powdered form. The solution should be warm (40°-50° C., approximately), when treated with base except that when the base is hydroxide or alkoxide, the solution should be cold to prevent hydrolysis. The preferred solid base to be employed in the inventive process is bicarbonate or carbonate due to its low cost and availability. Also, carbonate and bicarbonate are mild bases which substantially eliminate the chance of hydrolysis. Upon treatment with the base, a solid salt of aldonic acid is formed which may be isolated by filtration. The remaining solution contains the starting amine, the aldonamide and the organic solvent.

The combined recovered amine and aldonamide may be recycled (with or without the solvent) as the starting ingredients of the inventive process. The amine may be separated from the aldonamide by evaporating the solvent and washing the residue with a non-polar solvent, e.g. acetone or isopropanol. The aldonamide is left as the residue.

The solution may be treated with charcoal (if the solution is colored) before or after treatment with base.

The recovered solid salt of aldonic acid which has been filtered out is preferably then converted into aldonic acid by a variety of methods, for instance acidification with acids such as HCl, H$_2$SO$_4$ and the like. The preferred method of converting the salt into aldonic acid is by passing the salt through a cationic exchange column; this method is preferred because it avoids formation of NaCl and converts any NaOH present in the eluate to water. Suitable cationic exchange resin columns are as follows:

Dowex ® and Amberlite ®, such as Dowex ® and Amberlite IRP.69 ® and other strongly acidic resins.

In the inventive process, $R^1$ and $R^2$ groups on the starting amine, HNR$^1$R$^2$, are attached to the nitrogen of an aldonamide. Thus, depending on the particular amine employed, a variety of N-substituted aldonamides may be synthesized according to the inventive process. Preferably, in order to simplify synthesis and reduce cost, $R^1$ is hydrogen, thus a primary amine is employed. $R^1$ and/or $R^2$ generally contain up to 36 carbon atoms. For the sake of clarity, examples of various substituted aldonamides will be given below using lactobionamide of Formula A, maltobionamide of Formula B and gluconamide of Formula C as an illustration. The corresponding ammonium salts of lactobionamide, maltobionamide and gluconamide are illustrated by Formula D, Formula E, and Formula F, respectively.

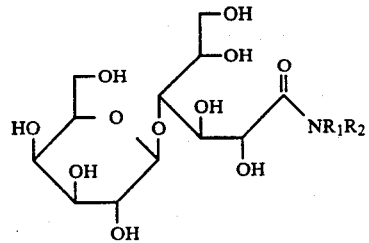

FORMULA A

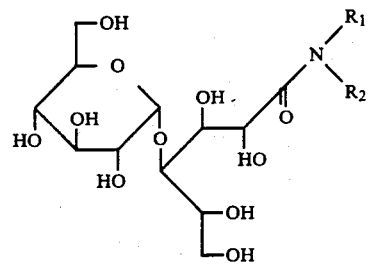

FORMULA B

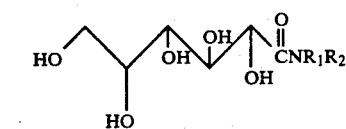

FORMULA C

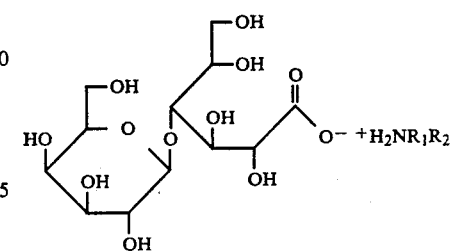

FORMULA D

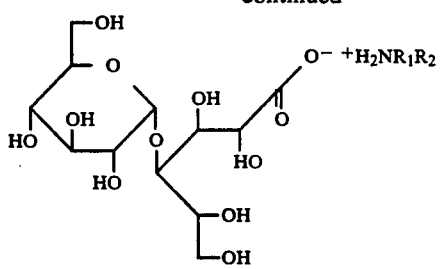

FORMULA E

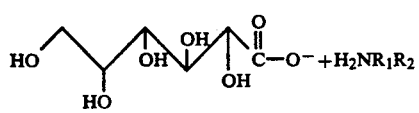

FORMULA F

N-alkyl lactobionamides are compounds of Formula A wherein $R^1$ and/or $R^2$ is an aliphatic hydrocarbon radical (which may include heteroatoms). Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, and octadecyl, and allyl, undecenyl, oleyl, linoleyl, linolenyl, propenyl, and heptenyl. The active compounds of the inventive compositions may contain straight or branched aliphatic groups. Aromatic radicals are exemplified by benzyl, aniline, or substituted benzyl or aniline groups. Suitable mixed aliphatic aromatic radicals are exemplified by benzyl, phenyl ethyl, phenoxy ethyl, and vinyl benzyl. Cycloaliphatic radicals are exemplified by but not limited to cyclopentyl and cyclohexyl.

N-lactobionyl aminoacid esters include but are not limited to esters of those amino acids which naturally occur in proteins, e.g. alanine, valine, glycine, lysine, leucine, arginine, aspartic acid, glutamic acid, asparagine, glutamine, threonine, serine, cysteine, histidine, tyrosine, methionine, as well as naturally occurring amino acids which are not found in proteins, such as β-alanine, sarcosine, gamma-aminobutyric acid, ornithene, citrulline, and the like. An example of N-lactobionyl amino acid ester is when in Formula A $R^1$ is hydrogen and $R^2$ is

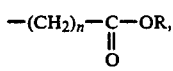

where n is an integer greater than 1 and R is for instance an aliphatic hydrocarbon radical containing up to 36 carbon atoms.

N-(alkyloxy)alkyl lactobionamides are exemplified but not limited to compounds wherein $R^1$ and/or $R^2$ is -$(CH_2)_n$—O—$R^6$, (an ether connected to amine, i.e., an "ether amine" group) wherein n is an integer equal to or greater than 1, preferably from 1 to 10 and $R^6$ is an aliphatic hydrocarbon radical, an aromatic radical, a cycloaliphatic radical as described above for $R^1$ and $R^2$. Preferably n is from 1 to 3 and $R^6$ is an aliphatic hydrocarbon radical containing 1 to 18 carbon atoms.

N-alkyl lactobionamides, N-(alkyloxy)alkyl lactobionamides and N-lactobionyl aminoacid esters typically contain up to 36 carbon atoms in $R^1$ and $R^2$ groups, preferably up to 24 carbon atoms, most preferably from 8 to 18 carbon atoms, and optimally from 10 to 16 carbon atoms in order to attain optimum surface activity.

N-(polyalkyloxy)alkyl lactobionamides are exemplified by but not limited to compounds wherein $R^1$ and/or $R^2$ is —$R^4$—$(OR^4)_n$—$R^4$—$R^5$ wherein n is an integer greater than 1, $R^4$ is selected from the group consisting of ethylene, propylene, and mixtures thereof; and $R^5$ is an amine or lactobionamide moiety. The number of repeating units in the alkylene oxide radical typically ranges from 2 to 10,000, preferably is from 2 to 100, most preferably from 2 to 10. $R^5$ is preferably lactobionamide (the resulting compound is N-(polyalkyloxy)alkyl (bis) lactobionamide) in order to provide an additional β-galactose moiety. $R^1$ and/or $R^2$ groups within N-(polyalkyloxy)alkyl lactobionamides may contain heteroatoms; for instance, $R^2$ may be —$CH_2CH_2$—S—$CH_2CH_2$—$(OCH_2OCH_2)_n$—S—$CH_2CH_2$—$R^5$.

Of course, other $R^1$ and $R^2$ radicals not listed above but within the scope of the claims may be employed.

N-substituted maltobionamides, cellobionamides, melibionamides, gentibionamides and other aldonamides analogous to N-substituted lactobionamides discussed in detail above may be produced according to the present invention, as long as a particular primary or secondary amine, which is necessary to deliver the desired $R^1$ and/or $R^2$ group to the nitrogen atom of the aldonamide is commercially available or can be synthesized.

The following specific examples further illustrate the present invention, but the invention is not limited thereto.

Dodecyl and tetradecylamines (99–96%) were obtained from Aldrich Chemicals and A.C.S. certified grade methanol which contained 0.02–0.1% of water was used.

EXAMPLE 1

Tetradecylammonium lactobionate

Lactobiono-1,5-lactone (20 g, 1 eq) was dissolved in water (150 ml) at 70° C. Tetradeoylamine (12.5 g, 1 eq) in 50 ml of methanol was added dropwise. The resulting solution was evaporated on a rotary evaporator to remove methanol. The resulting mixture was freeze-dried to give 30 grams of tetradecylammonium lactobionate. Tetradecylammonium lactobionate was characterized by NMR and mass spectroscopy.

N-tetradecyl lactobionamide

In a 5 L three necked round bottom flask equipped with a condenser and mechanical stirrer, lactobiono-1,5-lactone (400 g) was dissolved in warm methanol (3.5 L, 50°–55° C). Melted tetradecylamine (1.0 eq, 272 g) was then added gradually in 3 portions. The reaction was cooled to room temperature followed by stirring overnight to allow complete crystallization. The desired white product was filtered and recrystallized from methanol in 91% (550 g) isolated yield. The methanol filtrate contained a mixture of N-tetradecyl lactobionamide and tetradecylammonium lactobionate (identified by NMR and mass spectroscopy and by comparison with synthesized tetradecyl ammonium lactobionate).

EXAMPLE 2

Dodecylammonium lactobionate

Lactobiono-1,5-lactone (13.2 g, 1 eq) was dissolved in water (150 ml) at 70° C.; dodecyllamine (7.2 g, 1 eq) in 50 ml MeOH was added slowly. The resulting solution was rotary evaporated to remove MeOH, followed by freeze-drying to give 20g of dodecylammonium lactobionate. Dodecylammonium lactobionate was characterized by NMR and mass spectroscopy.

N-dodecyl lactobionamide

N-dodecyl lactobionamide was prepared according to the procedure described in Example 1 for N-tetradecyl lactobionamide. The isolated yield after recrystallization was 84%. The methanol filtrate contained a mixture of N-dodecyl lactobionamide and dodecylammonium lactobionate (identified by NMR and mass spectroscopy and by comparison with synthesized dodecyl ammonium lactobionate).

EXAMPLE 3

Comparative Example

In a three necked (5.0 L) round bottom flask equipped with a condenser and a mechanical stirrer, tetradecylamine (204 g, 1.0 eq) was dissolved in warm methanol (50° C., 1000 g). Lactobiono-1,5-lactone (300 g, 1.0 eq) was added and the reaction was heated at 70°-75° C. for one hour. Activated charcoal was added (40 g) and the solution was filtered hot. The solution was cooled overnight and the resulting product of yellow color was filtered and washed with methanol (750 ml), diethyl ether, (750 ml) and dried in vacuum at 40° C. The yield was about 51% after recrystallization.

Examples 1 and 2 demonstrate that a by-product obtained during the formation of N-substituted aldonamide is an ammonium salt of the aldonic acid. Examples 1 and 2 demonstrate that improved yields are obtained when aldono-1,5-lactone is first mixed with the solvent, and the amine is added subsequently and gradually, as compared to the procedure of Example 3 wherein tetradecylamine was dissolved first. Further, it can be seen from Examples 1 and 2 which are within the scope of the invention and from Example 3 which is not within the scope of the invention that the use of reaction temperature above 65° C. resulted in low yield and colored precipitate, while the use of reaction temperatures below 65° C. result in high yield of purer products.

EXAMPLE 4

Lactobiono-1,5-lactone (400g) was suspended in warm methanol (2 liters, 50° C.), cocoamine (Adogen 160-D ®, from Sherex, 207 g) was added in 5 equal portions over a 10 minute span. Stirring was continued for 10 minutes until a homogenous solution was obtained. The mixture was cooled to room temperature and seeded with small amount of coco lactobionamide. The reaction was left standing at room temperature overnight. The coco lactobionamide was filtered, washed with warm acetone (2×500ml) and dried in vacuum oven to obtain 395g of product.

The methanol filtrate was treated with 13g of powdered $K_2CO_3$ at 50° C. for 2 hours followed by filtration to remove potassium lactobionate (68g). The methanol filtrate was then treated with small amount of charcoal followed by activated molecular sieve. The methanol solution containing coco lactobionamide and coco amine can be recycled.

EXAMPLE 5

The procedure employed in Example 4 was repeated except that NaOH was employed instead of $K_2CO_3$.

EXAMPLE 6

The procedure employed in Example 4 was repeated except that KOH was employed instead of $K_2CO_3$.

EXAMPLE 7

The procedure employed in Example 4 for synthesis of coco lactobionamide was repeated except that $KHCO_3$ was employed instead of $K_2CO_3$.

$KHCO_3$ was preferred because no hydrolysis of the coco lactobionamide was observed. Some hydrolysis of coco lactobionamide occurred with treatment of $K_2CO_3$, NaOH and KOH.

EXAMPLE 8

Glucono-1,5-lactone (50 g) was dissolved in warm methanol (150ml, 45° C.), decylamine (47.7g, 1 eq.) was added slowly in several portions. Stirring was continued for 10 minutes. The mixture was cooled to room temperature with stirring overnight. The product was filtered, washed with acetone and dried in vacuum oven at 40° C.

The methanol filtrate is treated with 1.4g of powdered $KHCO_3$ at 50° C. for 2 hours followed by filtration to remove potassium gluconate. The methanol filtrate is then treated with small amount of charcoal followed by activated molecular sieve. The methanol solution containing N-decyl gluconamide and decylamine can be recycled.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

We claim:

1. A process of preparing an N-substituted aldonamide, the process comprising the steps of:
   i) preparing a homogeneous mixture comprising an aldonolactone, an organic polar solvent, and an amine $HNR^1R^2$, wherein $R^1$ and $R^2$ are the same or different and may contain heteroatoms, selected from the group consisting of nitrogen, oxygen, and sulphur, and are selected from the group consisting of hydrogen, an aliphatic hydrocarbon radical, an aromatic radical, a cycloaliphatic radical, an amino acid ester, an ether amine and mixtures thereof, except that $R^1$ and $R^2$ are not both hydrogen at the same time, wherein the total number of carbon atoms in $R^1$ and $R^2$ ranges from 1 to 36 and wherein the molar ratio of the aldonolactone to the amine is in the range of from abut 1:1.5 to about 1:1.
   ii) reacting the homogeneous mixture at a temperature in the range of from about 25° C. to not greater than 65° C. to obtain a reaction product including a first solution comprising the aldonamide and a corresponding ammonium salt of an aldonic acid; and
   iii) treating the first solution with a solid base to obtain a solid salt of aldonic acid and a second solution comprising the starting amine and the aldonamide, wherein the base and the salt are solid at ambient temperature and pressure.

2. The process of claim 1 further comprising filtering out the solid salt of aldonic acid obtained in step (iii) and converting the salt to an aldonic acid.

3. The process of claim 2 wherein the aldonic acid salt is converted to the aldonic acid by passing the salt through a cationic exchange column.

4. The process of claim 3 further comprising preparing the aldonolactone from the aldonic acid.

5. The process of claim 1 further comprising the steps of removing the polar organic solvent from the second solution obtained in step (iii) to obtain the residue and washing the residue with a non-polar solvent to obtain the starting amine.

6. The process of claim 1 wherein the reaction product in step (ii) further comprising a precipitate of the aldonamide.

7. The process of claim 6 further comprising separating the precipitate from the solution.

8. The process of claim 1 wherein the mixing is conducted at a temperature in the range of from 25° C. to 65° C.

9. The process of claim 1 wherein the aldonolactone is an aldono-1,5-lactone.

10. The process of claim 1 wherein the reaction in step (ii) is conducted at a temperature in the range of from 25° C. to 50° C.

11. The process of claim 1 wherein the solid base is selected from the group consisting of inorganic bicarbonate salts, inorganic carbonate salts, inorganic hydroxides, and metal alkoxide mixtures thereof.

12. The process of claim 1 further comprising recycling the second solution obtained in step (iii) as part of the starting material mixture.

13. The process of claim 1 wherein $R^1$ is hydrogen.

14. The process of claim 1 wherein the aldonamide is selected from the group consisting of lactobionamides, maltobionamides, cellobionamides, melibionamides, and gentiobionamides.

15. The process of claim 1 wherein $R^1$ is hydrogen and $R^2$ is an aliphatic hydrocarbon radical containing from 1 to 36 carbon atoms.

16. The process of claim 1 wherein the aldonamide is N-alkyl lactobionamide.

17. The process of claim 16 wherein N-alkyl lactobionamide has an alkyl chain having from 1 to 20 carbon atoms.

* * * * *